United States P...
Bjorklund et al.

4,105,337

Aug. 8, 1978

[54] SELF-INDUCED ROTA....
ELLIPSOMETER

[75] Inventors: Gary Carl Bjorklund, West Windsor; Paul Foo-Hung Liao, Middletown, both of N.J.

[73] Assignee: Bell Telephone Laboratories, Incorporated, Murray Hill, N.J.

[21] Appl. No.: 795,740

[22] Filed: May 11, 1977

[51] Int. Cl.² ............................................. G02F 1/00
[52] U.S. Cl. .................................. 356/114; 350/147; 356/116
[58] Field of Search ..................... 356/114, 116, 117; 350/147

[56] References Cited
U.S. PATENT DOCUMENTS 3,864,020  2/1975  Armstrong et al. ................. 350/147

.................... 350/147

OTHER PUBLICATIONS

Levenson et al., "Raman-Induced Kerr Effect with Elliptical Polarization," J. Opt. Soc. Am., vol. 66, No. 7, Jul. 1976, pp. 641-643.

*Primary Examiner*—John K. Corbin
*Assistant Examiner*—R. A. Rosenberger
*Attorney, Agent, or Firm*—Daniel D. Dubosky

[57] ABSTRACT

The invention relates to an ellipsometer for measuring the degree of elliptical polarization of a beam of coherent optical radiation. Applications of the invention include a device for measuring birefringence and a material detector for measuring small concentrations of substances in a gaseous medium.

7 Claims, 2 Drawing Figures

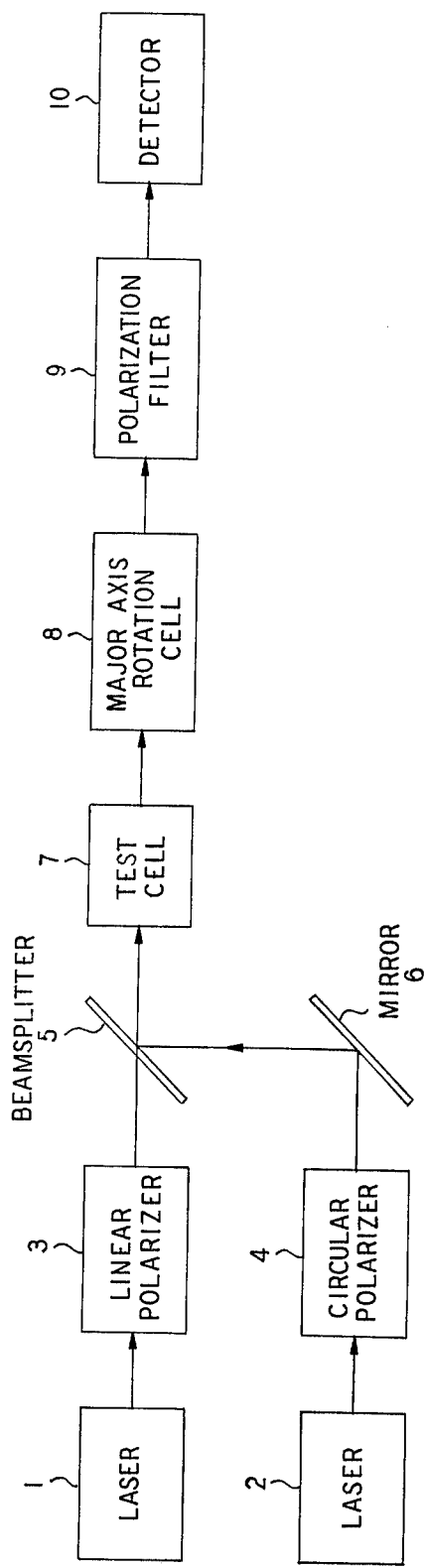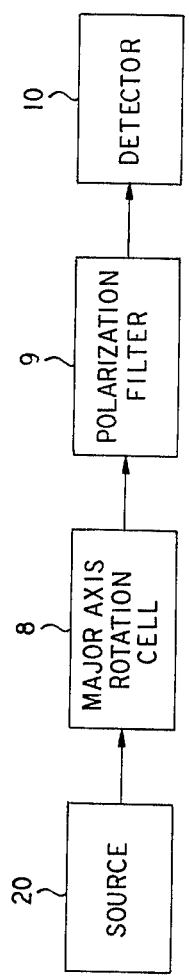

SELF-INDUCED ROTATION ELLIPSOMETER

BACKGROUND OF THE INVENTION

Previous work with lasers in the field of material detection has been in the nature of tuning the laser beam across a single photon resonance of the material being detected and measuring the amount of power absorbed or scattered from the incident beam. This technique is rather insensitive and is subject to background, since other materials may also remove power from the beam.

The previous method of detection of elliptical polarization has merely been to rotate a polarization filter and measure the power transmitted as a function of angle. Since no polarization filter is perfect, there is a finite amount of power transmitted by a filter at a right angle to the plane of polarization of a linear beam and even a perfectly polarized linear beam will appear to be slightly elliptically polarized. This method also lacks sensitivity.

SUMMARY OF THE INVENTION

The invention relates to a device for measuring the degree of elliptical polarization of a coherent beam of optical radiation. It makes use of a self-induced ellipse rotation effect that takes place when the frequency of the elliptically polarized beam is close to the frequency of a strong single photon resonance of a medium.

In an application as a pollution detector, elliptical polarization is induced in a linearly polarized beam by passing the linearly polarized beam to be tested in coincidence with a circularly polarized beam through a sample of a gaseous medium. When the frequencies of the two beams add (or subtract) to a value close to the frequency associated with a two-photon (or Raman) resonance of the pollutant that is to be measured, the two beams interact in such a way that the initially linearly polarized beam becomes slightly elliptically polarized, the degree of ellipticity being dependent on the concentration of the material in question. The major axis of the elliptically polarized beam so produced is then rotated by the ellipse rotation effect described above by coupling the beam through a cell having a medium with an appropriate single photon resonance. The rotated elliptically polarized beam passes through a polarization filter oriented at right angles to the initial direction of linear polarization. The amount of radiation transmitted by the filter depends on the amount of ellipticity, and thus on the concentration of the pollutant that it is desired to measure.

The rotation effect serves to increase the sensitivity of the material detector. A small portion of the elliptically polarized beam (depending on the magnitude of the minor axis of the ellipse) would be transmitted by the filter even in the absence of the ellipse rotation. The rotation of the axis of the ellipse increases the amount of radiation transmitted and thus increases the sensitivity of the device by producing a greater amount of transmitted power for a given concentration of pollutant.

The device is also applicable, of course, for the measurement of the concentration of desired materials as well as of pollutants.

BRIEF DESCRIPTION OF THE DRAWINGS

FIG. 1 shows in partially schematic, partially pictorial form a material detector according to the invention.

FIG. 2 shows in partially schematic, partially pictorial form an ellipsometer according to the invention.

DETAILED DESCRIPTION

In FIG. 1, laser 1 generates a beam at a frequency that is close to the frequency of a single-photon resonance of the material in major axis rotator 8, illustratively the sodium vapor. The beam is polarized along a predetermined direction by linear polarizer 3, passes through beamsplitter 5 and enters test cell 7 simultaneously with the beam from laser 2.

Laser 2 generates a beam at a frequency such that the sum (or difference) of frequencies of the beams of lasers 1 and 2 is close to the frequency associated with a selected two-photon (or Raman) resonance of the material being tested. The beam from laser 2 is circularly polarized by polarizer 4 and is reflected by mirror 6 and beamsplitter 5 so that it enters test cell 7 collinearly and simultaneously with the linear beam from laser 1.

Test cell 7 contains the material to be tested, illustratively a sample of a gaseous mixture such as air. The sum (or difference) of the frequencies of the two laser beams is set to a value close to the value associated with a selected two-photon (or Raman) resonance of some pollutant, such as carbon monoxide. If no carbon monoxide is present in the sample being tested, the linearly polarized beam is unaffected as it passes through test cell 7. In that case, the linearly polarized beam is not affected by major axis rotation cell 8, which acts only on elliptically polarized beams, and passes through cell 8 to polarization filter 9, the axis of which is set at a right angle to the direction of polarization of the beam. Since the respective axes of polarization of beam and filter are at right angles, the beam is blocked by the filter.

If some carbon monoxide is present in test cell 7, then the circularly polarized beam from laser 2 interacts with that component of the linearly polarized beam that satisfies the relevant angular momentum quantum mechanical selection rule. With the quantum mechanical selection rule satisifed, some fraction of that component of the linear beam will be absorbed, the amount absorbed being dependent on the density of carbon monoxide present in test cell 7. As the formerly linearly polarized beam leaves test cell 7, the two circularly polarized components of that beam will no longer be equal in amplitude, since one has been partially absorbed, and the beam will no longer be linearly polarized but will be elliptically polarized.

In major axis rotation cell 8, the two components of the elliptically polarized beam interact with the sodium vapor unequally, the precise strength of the interaction being dependent on how close the frequency of the beam is to the frequency associated with the resonance mentioned above (the well-known sodium-D line), the effect of this unequal interaction being to rotate the major axis of the elliptically polarized beam. The effect of this rotation on the amount of radiation passing through polarizing filter 9 is to increase it by a large amount. If major axis rotation cell 8 were not present, a small amount of light would pass through filter 9, and be detected in detector 10 the amount of light being dependent on the magnitude of the minor axis of the ellipse. When the major axis is rotated, the amount of light transmitted will be much larger than in the unrotated case, and detector 10 (having a particular sensitivity) will be able to detect far smaller quantities of carbon monoxide.

The increase of sensitivity of a detector constructed according to this invention over the sensitivity of a prior art detector may be illustrated by a numerical example, using sodium as the medium in the major axis rotation cell (at a density of $10^{14}/cm^3$) and a detuning of 1 GHz of the frequency of laser 1 from the sodium-D line.

The major axis will be rotated by an angle $$\Phi = \frac{16\pi^3 lN}{h^3 c^2} \frac{\mu_{12}^4}{(\Delta\nu)^3} \nu I_R \qquad (1)$$

where $l$ is the length of the major axis rotation cell, $\mu$ is the sodium vapor density, $\nu$ is the frequency of laser 1, $\Delta\nu$ is the detuning of laser 1 from the D resonance, $\mu_{12}$ is the dipole moment of the resonance, $h$ is Planck's constant, $c$ is the speed of light, and $I_R$ is the extra intensity of the stronger circularly polarized component of the elliptically polarized beam. If we assume confocal focusing, $$I_R = \frac{4P_R \nu}{lc} \qquad (2)$$

where $P_R$ is the extra power in watts. Substituting in Equation (1), we have:

$$\Phi(\text{radians}) = 1.2 \times 10^4 P_R(\text{watts}). \qquad (3)$$

The maximum $P_R$ may be expressed as:

$$P_R = \frac{nh\nu}{T} \qquad (4)$$

where $T$ is the lifetime of the level involved in the two-photon transition ($10^{-8}$ sec.), n is the number of molecules of pollutant per cubic centimeter, and the other symbols have been defined.

Substituting for $\Phi$ and squaring, we have $$\Phi^2 = 16 \times 10^{-14} n^2. \qquad (5)$$

The limit of detection of $\Phi$ is $\Phi^2 = 10^{-7}$ (see "Doppler-Free Laser Polarization Spectroscopy", by C. Wieman and T. W. Hänsch in *Physical Review Letters*, 36, 1170 (1976)), so the minimum amount of pollutant that may be detected is $n = 8 \times 10^2$ molecules. In a cell 10 centimeters long with confocal focusing, this corresponds to a density of approximately $3 \times 10^5$ molecules/$cm^3$.

Since air has a density of approximately $3 = 10^{19}$ molecules/$cm^3$, contaminants present in the ratio of one part in $10^{14}$ may be detected. The best measurement with absorption techniques that has come to our attention had a sensitivity of $10^{10}$ molecules/$cm^3$ ("Measurement of Sodium-Vapor-Density at Very Low Pressures by an Optical Method", by N. Ioli et al., *Journal of the Optical Society of America*, 61, 1251, (1971)). Accordingly, the present invention provides a factor of 30,000 increase in sensitivity.

This same amplification process of major axis rotation cell 8 can be used to measure the ellipticity of a beam produced by any other means, such as a pattern of birefringence induced by stress in an optical element and cell 8 can be used in connection with polarization filter 9 to measure ellipticity in the apparatus shown in FIG. 2. Source 20 produces a beam of radiation, the ellipticity of which is to be measured. The beam passes through major axis rotator 8 and polarization filter 9, as before, continuing on to detector 10. If source 20 is tunable, the frequency of the beam is tuned off resonance so the beam passes through cell 8 unaffected and filter 9 is rotated to measure the major and minor axes of the ellipse by observation of the signal in detector 10. Filter 9 is set along the minor axis (i.e., at a right angle to the major axis) and the frequency is tuned through the resonance. The signal in detector 10 is then a measure of the degree of rotation of the major axis and thus a measure of the ellipticity.

What is claimed is:

1. A material detector comprising:
    means for producing a first coherent optical beam at a first frequency, linearly polarized at a first angle,
    means for producing a second, circularly polarized, coherent optical beam at a second frequency,
    a test cell for holding a sample to be tested for the presence of said material,
    means for transmitting collinearly said first and second beams through said test cell, whereby said first beam becomes elliptically polarized, having major and minor axes, when a quantity of said material is present in said test cell and the sum of said first and second frequencies is substantially equal to the frequency associated with a two-photon resonance of said material,
    a major axis rotation cell containing a medium,
    means for extracting said first beam from said test cell and for transmitting said first beam through said major axis rotation cell, whereby said major axis is rotated to a second angle by the interaction of said first beam with said medium, and
    a polarization filter having an axis, intercepting said first beam after it has passed through said major axis rotation cell, which axis is oriented substantially at a right angle to said first angle, whereby said first beam is transmitted by said polarization filter only when said material is present in said test cell.

2. A material detector according to claim 1 in which said second frequency is tunable.

3. A material detector according to claim 2 in which said medium is an alkali metal vapor.

4. A material detector according to claim 3 in which said medium is sodium vapor.

5. An apparatus for measuring elliptical polarization of a beam of optical radiation comprising:
    a major axis rotation cell containing a medium having a strong single-photon resonance,
    means for transmitting a beam of elliptically polarized optical radiation of a predetermined frequency close to the frequency associated with said single-photon resonance into said major axis rotation cell,
    a polarization filter having an axis, which axis is rotatable about the direction of transmission of said optical beam, and
    means for extracting said optical beam from said major axis rotation cell and for directing said optical beam into said filter whereby a portion of said optical beam is transmitted by said filter, which portion varies as said axis is rotated about said direction of transmission.

6. An apparatus for measuring elliptical polarization according to claim 5 in which said medium is an alkali metal vapor.

7. An apparatus for measuring elliptical polarization according to claim 6, in which said medium is sodium vapor.

* * * * *